US012605395B2

(12) United States Patent
Qi et al.

(10) Patent No.: US 12,605,395 B2
(45) Date of Patent: Apr. 21, 2026

(54) MATERIALS AND METHODS FOR IMMUNOSUPPRESSIVE TUMOR MICROENVIRONMENT-TARGETED CANCER THERAPY

(71) Applicant: University of Cincinnati, Cincinnati, OH (US)

(72) Inventors: Xiaoyang Qi, Cincinnati, OH (US); Subrahmanya Duttu Vallabhapurapu, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 725 days.

(21) Appl. No.: 17/913,976

(22) PCT Filed: Apr. 1, 2021

(86) PCT No.: PCT/US2021/025303
§ 371 (c)(1),
(2) Date: Sep. 23, 2022

(87) PCT Pub. No.: WO2021/202826
PCT Pub. Date: Oct. 7, 2021

(65) Prior Publication Data
US 2023/0119248 A1 Apr. 20, 2023

Related U.S. Application Data

(60) Provisional application No. 63/003,509, filed on Apr. 1, 2020.

(51) Int. Cl.
| | |
|---|---|
| *A61K 38/18* | (2006.01) |
| *A61K 9/127* | (2025.01) |
| *A61K 31/683* | (2006.01) |
| *A61K 45/06* | (2006.01) |
| *A61K 47/62* | (2017.01) |
| *A61P 35/00* | (2006.01) |

(52) U.S. Cl.
CPC ............ *A61K 31/683* (2013.01); *A61K 45/06* (2013.01); *A61K 47/62* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 9,629,804 B2 | 4/2017 | Heartlein et al. | |
| 2010/0311844 A1 | 12/2010 | Qi et al. | |
| 2015/0272885 A1 | 10/2015 | Ashley et al. | |
| 2015/0272980 A1* | 10/2015 | Rodrigueza ............ | A61K 45/06 424/174.1 |
| 2018/0161272 A1* | 6/2018 | Obaid ................... | A61K 9/127 |

FOREIGN PATENT DOCUMENTS

| | | |
|---|---|---|
| CN | 108926535 A | 12/2018 |
| WO | 2019051149 A1 | 3/2019 |

OTHER PUBLICATIONS

EP Extended European Search Report dated Dec. 11, 2023 pertaining to EP application No. 21781580.2 filed Sep. 27, 2022, pp. 1-9.
International Search Report mailed Jul. 19, 2021 in reference to co-pending Application No. PCT/US2021/025303 filed Jun. 4, 2021.
Written Opinion mailed Jul. 19, 2021 in reference to co-pending Application No. PCT/US2021/025303 filed Jun. 4, 2021.
Yamamato, et al., Gastroenterol Res Pract, 2010, 240365, 2010.
Jematsu, et al. Handb Exp Pharmacol 183, 1-20, 2008.
Hashimoto, et al., J Biol Chem 278, 44205-44213, 2003.

* cited by examiner

*Primary Examiner* — Kortney L. Klinkel
*Assistant Examiner* — Alison Azar Salamatian
(74) *Attorney, Agent, or Firm* — DINSMORE & SHOHL LLP

(57) ABSTRACT

Many tumors induce and maintain an immunosuppressive tumor microenvironment (TME) that enables tumor to escape host immune system. The present disclosure identifies that cancer cells secrete exosome/microparticle-free, soluble, phosphorylated Hsp70 (pHsp70) (Heat Shock Protein 70 (Hsp70))), which triggers macrophage (M) M2 polarization. It is a further aspect that lipid nanovesicles (NVs) made of dioleoylphosphatidylglycerol (DOPG) and of DOPG complexed with saposin C (SapC) bind to cancer secreted Hsp70, inhibit M differentiation and polarization, and reduce tumor growth. In addition, administration of DOPG-NVs rendered monocytes insensitive to TLR2 (Toll Like Receptor 2) and TLR6 (Toll Like Receptor 6) ligands, suggesting that administration of DOPG-NVs interferes with TLR function.

19 Claims, 12 Drawing Sheets

Specification includes a Sequence Listing.

A

B

C

D

E

A

B

SapC                                    DOPG                    SapC-DOPG

A kDa

75 —

← Hsp70

| | | |
|---|---|---|
| + | + | SC Lysate |
| - | + | TLR2 IP |
| + | - | IgG IP |
| + | + | Gli36 CM |

B

C

D Mouse tumor MØs

SEQUENCE LISTING

<160> NUMBER OF SEQ ID NOS: 1

<210> SEQ ID NO 1
<211> LENGTH: 80
<212> TYPE: PRT
<213> ORGANISM: Homo sapiens

<400> SEQUENCE: 1

```
Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln
        35                  40                  45
```

-continued

---

```
Glu Val Val Asp Thr Tyr Gly Ser Ser Ile Leu Ser Ile Leu Leu Glu
    50              55              60

Glu Val Ser Pro Glu Leu Val Cys Ser Met Leu His Leu Cys Ser Gly
65              70              75              80
```

MATERIALS AND METHODS FOR IMMUNOSUPPRESSIVE TUMOR MICROENVIRONMENT-TARGETED CANCER THERAPY

CROSS-REFERENCE TO RELATED APPLICATIONS

This application is a U.S. National Stage Entry under 35 U.S.C. 371 of International Patent Application No. PCT/US2021/025303, filed Apr. 1, 2021, which claims priority to U.S. Provisional Patent Application 63/003,509, filed Apr. 1, 2020, the contents of which are hereby incorporated by reference in their entirety.

FIELD OF THE INVENTION

This disclosure relates to the identification of a pathway of immunosuppression caused by tumor cells in the tumor microenvironment and to methods of administering therapeutic that disrupt the identified pathway.

SEQUENCE LISTING

A sequence listing in ASCII format, having file name [0002.1] "10738860SEQLIST_ST25.txt" (1058 bytes), created on Apr. 1, 2021, is incorporated herein by reference.

BACKGROUND

Recent advances in cancer studies have identified the importance of the tumor microenvironment (TME) or area immediately surrounding the tumor cells. While the environment itself is not directly affected by the genetic aberrations causing the tumor to grow, it is now understood that the tumor cells will communicate with the TME and attempt to cause any changes therein that might benefit tumor growth and progression. One particular area of interest is the ability of a tumor to regulate or control any possible immunogenic response to the tumor growth in the TME which might otherwise recognize the growth and respond positively. There is therefore a need to identify and interfere with signaling between the tumor and the TME to disrupt immunosuppression therein.

SUMMARY OF THE INVENTION

The present disclosure concerns the identification that lipid nanovesicles (NVs) can inhibit immunosuppression by the tumor microenvironment (TME). In some aspects, the present disclosure concerns methods for treating a cancerous or pre-cancerous cell by administering to the cell a therapeutically effective amount of nanovesicles comprised of dioleoylphosphatidylglycerol (DOPG). In further aspects, the nanovesicles may further include saposin C (SapC). In certain aspects, the present disclosure concerns administration of a combination of DOPG and SapC-DOPG nanovesicles. In certain aspects, the cell is in vitro. In other aspects, the cell is in vivo.

In some aspects, the methods of the present disclosure further include administering an additional chemotherapeutic to the cell. By way of example, such additional chemotherapeutic may include one or more of everolimus, erlotinib, 5-fluorouracil, irinotrecan, olaparib, mitomycin, paclitaxel, sunitinib, FOLFIRINOX, cisplatin, oxaliplatin, lanreotide, lutetium Lu 177-dotatate, bevacizumab, carmustine, naxitamab, lomustine, temozolomide, afatinib, alectinib, pemetrexed, brigatinib, atezolizumab, capmatinib, carboplatin, cemoplimab, ceritinib, crizotinib, ramucirumab, dabrafenib, docetaxel, doxorubicin, durvalumab, entrectinib, pralsetinib, gefitinib, gemcitabine, ipilimumab, pembrolizumab, lorlatinib, trametinib, methotrexate, necitumumab, nivolumab, osimertinib, selpercatinib, tepotinib, trametinib, vinorelbine, or a combination thereof.

In some aspects, the present disclosure concerns methods for treating cancer in a subject, comprising administering a combination of a therapeutically effective amount of nanovesicles comprised of dioleoylphosphatidylglycerol (DOPG) to the subject. In some aspects, the nanovesicles further include SapC. In some aspects the NVs may be of only DOPG or only of SapC-DOPG. In further aspects, a combination of SapC-DOPG and DOPG NVs may be administered.

In some aspects, the present disclosure concerns methods for treating cancer in a subject, by administering a combination of a therapeutically effective amount of nanovesicles comprised of DOPG and/or SapC-DOPG to the subject and administering an additional chemotherapeutic or therapy to the subject. The additional chemotherapeutic may be administered simultaneously with the NVs, sequentially with the NVs, and/or asynchronously as the NVs. In some aspects, the additional chemotherapeutic may be one or more of everolimus, erlotinib, 5-fluorouracil, irinotrecan, olaparib, mitomycin, paclitaxel, sunitinib, FOLFIRINOX, cisplatin, oxaliplatin, lanreotide, lutetium Lu 177-dotatate, bevacizumab, carmustine, naxitamab, lomustine, temozolomide, afatinib, alectinib, pemetrexed, brigatinib, atezolizumab, capmatinib, carboplatin, cemoplimab, ceritinib, crizotinib, ramucirumab, dabrafenib, docetaxel, doxorubicin, durvalumab, entrectinib, pralsetinib, gefitinib, gemcitabine, ipilimumab, pembrolizumab, lorlatinib, trametinib, methotrexate, necitumumab, nivolumab, osimertinib, selpercatinib, tepotinib, trametinib, vinorelbine, or a combination thereof. In some aspects, the additional therapy may be one or more of antibody therapy, gene silencing therapy, vaccine therapy, or radiation therapy.

In some aspects, the present disclosure concerns methods for treating pancreatic cancer in a subject, by administering a combination of a therapeutically effective amount of nanovesicles comprised of DOPG and/or SapC-DOPG to the subject.

In some aspects, the present disclosure concerns methods for treating glioblastoma in a subject, by administering a combination of a therapeutically effective amount of nanovesicles comprised of DOPG and/or SapC-DOPG to the subject.

In some aspects, the present disclosure concerns methods for treating lung cancer in a subject, by administering a combination of a therapeutically effective amount of nanovesicles comprised of DOPG and/or SapC-DOPG to the subject.

In some aspects, the present disclosure concerns methods for treating cancer in a subject, by administering a combination of a therapeutically effective amount of nanovesicles comprised of DOPG and/or SapC-DOPG to the subject, wherein the nanovesicles are administered in a plurality of doses over a treatment period. In some aspects, the treatment period may be of from about 14 to about 40 consecutive days.

In some aspects, the present disclosure concerns methods for treating cancer in a subject, by administering a combination of a therapeutically effective amount of nanovesicles comprised of DOPG and/or SapC-DOPG to the subject, wherein the nanovesicles are administered in a dose of from about 0.3 mg/kg to about 12 mg/kg.

DETAILED DESCRIPTION

Figure 1:
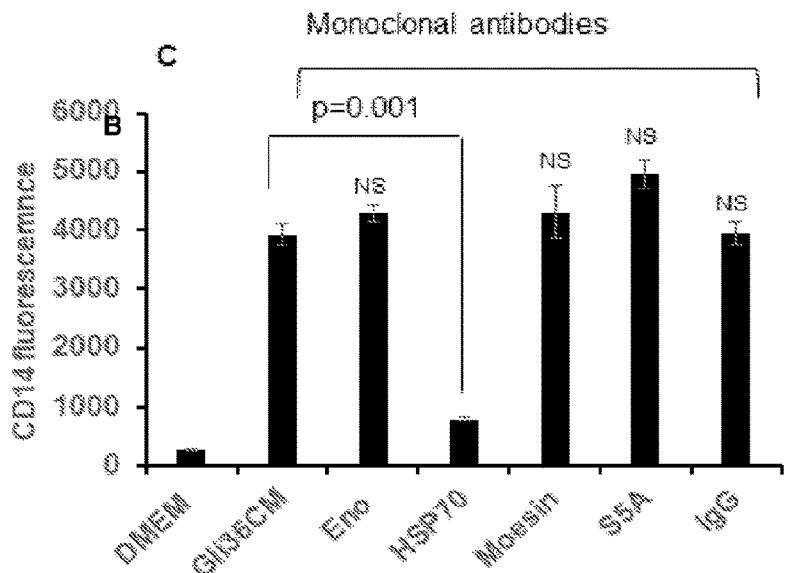
FIG. 1 shows that the macrophage differentiation factor in conditioned media (CM) is the protein Hsp70. A shows Gli36 CM loses its THP-1 differentiation activity upon proteinase K treatment. B shows proteins identified through LC-MS analyses of Gli36 CM C shows neutralizing antibodies against indicated protein reveal specific requirement of Hsp70 in CM to induce THP-1 differentiation.

The present disclosure relates to the identification of mechanism of polarization of a macrophage (MØ) in the tumor microenvironment (TME) through the secretion of heat shock protein 70 (Hsp70) by the tumor cells into the TME. In some aspects, the present disclosure concerns identification of how the cancer-secreted phosphorylated Hsp70 polarizes MØs in the TME and leads to suppression of any potential immune response to the tumor cells. In some aspects, the present disclosure also concerns identified methods of inhibiting and/or disrupting the polarization of MØs through the administration and/or treatment of the TME and/or tumor with a lipid nanovesicle (NV). In some aspects, the lipid nanovesicle is made of DOPG (dioleoylphosphatidylglycerol). In further aspects, the lipid nanovesicle is conjugated and/or associated with the peptide of Saposin C (SapC).

The following description of particular aspect is merely exemplary in nature and is in no way intended to limit the scope of the disclosure, its application, or uses, which may, of course, vary. The disclosure is described with relation to the non-limiting definitions and terminology included herein. These definitions and terminology are not designed to function as a limitation on the scope or practice thereof but are presented for illustrative and descriptive purposes only.

The terminology used herein is for the purpose of describing particular aspects only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some aspects ±20%, in some aspects ±10%, in some aspects ±5%, in some aspects ±1%, in some aspects ±0.5%, and in some aspects ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise defined, all terms (including technical and scientific terms) used herein have the same meaning as commonly understood by one of ordinary skill in the art to which this disclosure belongs. It will be further understood that terms such as those defined in commonly used dictionaries should be interpreted as having a meaning that is consistent with their meaning in the context of the relevant art and the present disclosure, and will not be interpreted in an idealized or overly formal sense unless expressly so defined herein.

Figure 7:
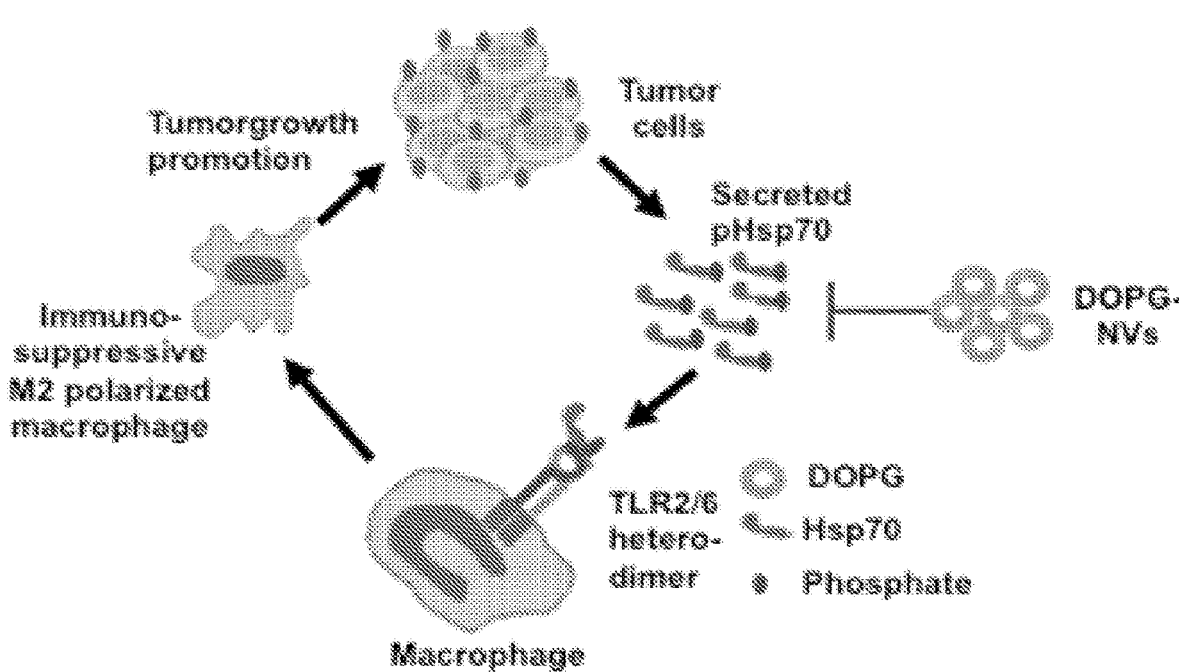
FIG. 7 shows secretion of phospho-Hsp70 by cancer cells, its binding to TLR2/TLR6 dimer on MØs, followed by induction of M2 polarization of tumor associated MØs (TAMs), induction of immunosuppressive TME, facilitating tumor growth. DOPG-NVs acting on the tumor secreted pHsp70, to block the whole pathway of immunosuppression

In some aspects, the present disclosure concerns the administration of lipid nanovesicles (NVs) to tumor cells. In some aspects the NVs are made of DOPG (dioleoylphosphatidylglycerol) and/or of saposin C (SapC) conjugated DOPG NVs. As identified herein, the NVs when administered to a tumor cell or the TME overcome or reduce immunosuppression in the TME. In some other aspects, the present disclosure concerns the identification of an immunosuppressive pathway between tumor cells and the TME. As identified herein, by introducing media conditioned by tumor cells to monocytes, it was observed that factors released into the conditioned media (CM) by tumor cells induced differentiation of the monocytes into macrophages. The ability to induce differentiation was however absent when the conditioned media (CM) was pre-treated with a proteinase, indicating the factor(s) responsible were proteins (see, e.g., FIG. 1). Through depletion of possible proteins, it was identified that Hsp70 was the released protein chiefly responsible for inducing the differentiation into macrophages. It was also confirmed that the tumor cell secreted Hsp70 was heavily phosphorylated (pHsp70=phosphorylated-Hsp70). When the CM was pre-treated with a phosphatase to remove attached phospho groups from pHsp70, the resulting CM was significantly reduced in its ability to induce differentiation into macrophages, indicating differentiation is dependent on the phosphorylation status of the tumor cell secreted Hsp70. As further set forth in FIG. 7, the pHsp70 uses dimerized toll-like receptors (TLRs) 2 and 6 on the monocyte, leading to differentiation into M2 polarized macrophages that inhibit immunity against a tumor and promoted tumor growth.

Figure 3:
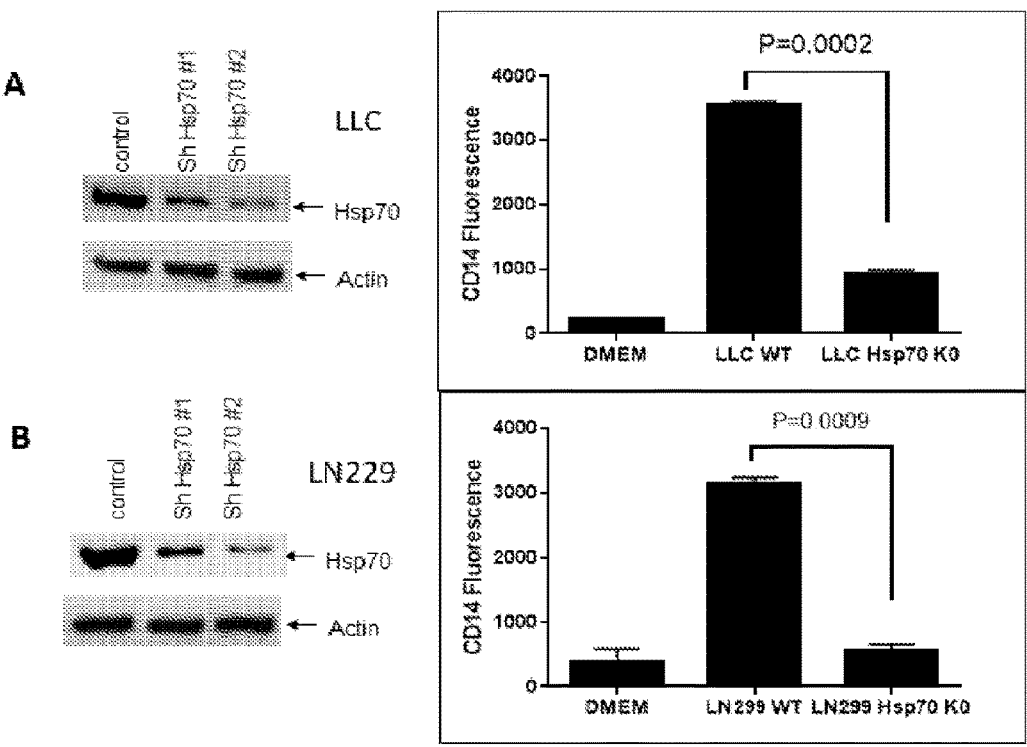
FIG. 3 shows knockdown of Hsp70 leads to reduction in macrophage differentiation capacity of CM, reduction in tumor growth and alters polarization of tumor associated MØs. A shows knockdown of Hsp70 in LLC cells (left panel) and reduction of THP-1THP-1 differentiation capacity of CM upon Hsp70 knockdown (right panel). B shows knockdown of Hsp70 in LN229 cells (left panel) and reduction of THP-1THP-1 differentiation capacity of CM upon Hsp70 knockdown (right panel). C shows MØs from subcutaneous tumors from WT LLC cells expressing control ShRNAS, showing predominantly CD206 positive M2 MØs and minimal iNOS positive M1 MØs. D shows MØ s from subcutaneous tumors from Hsp70 knock down LLC cells showing predominantly iNOS positive M1 MØs and minimal CD206 positive M2 MØs. E & F show graphical representation of C&D. G shows tumor growth curves of LLC subcutaneous tumors from LLC WT cells and Hsp70 knockdown LLC cells.
Figure 3:
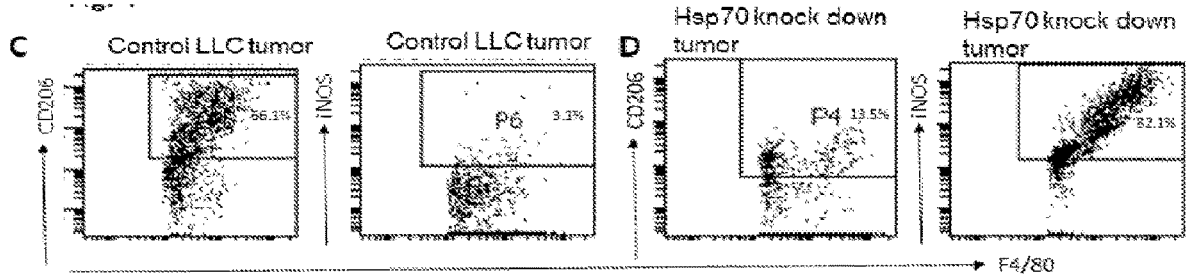
Figure 3:
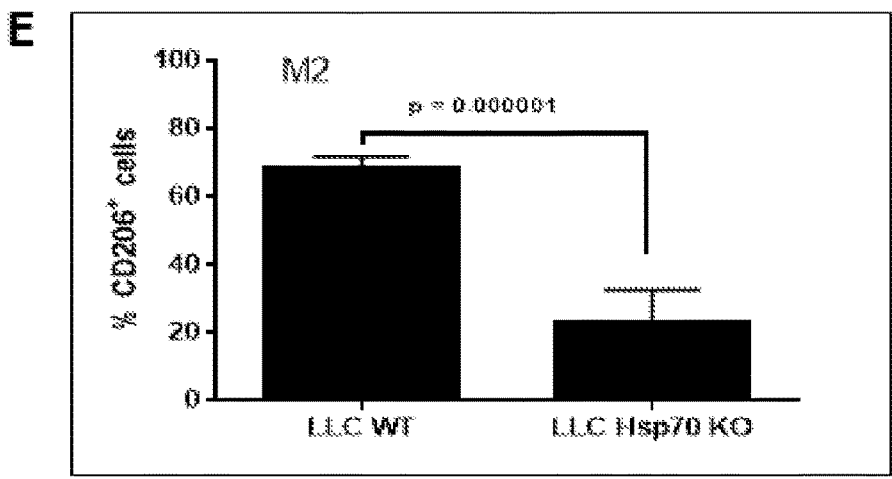
Figure 3:
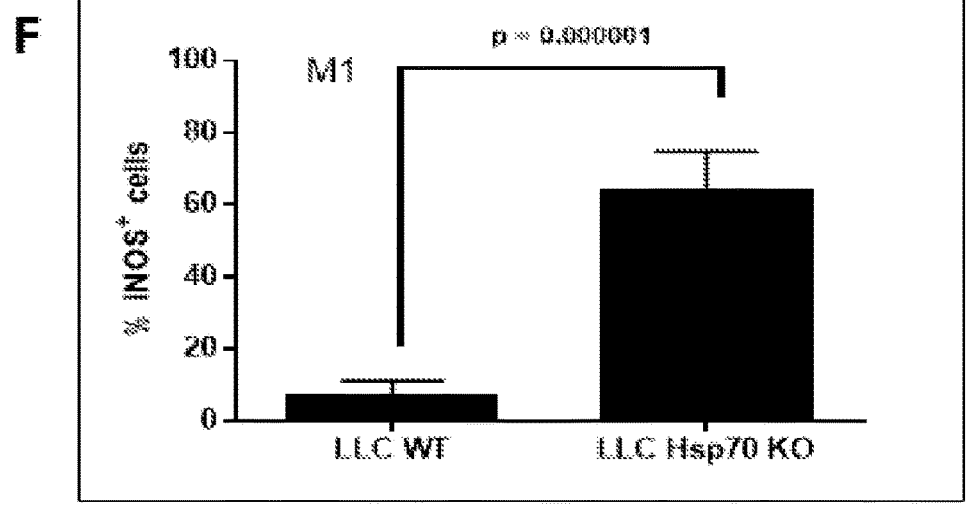
Figure 3:
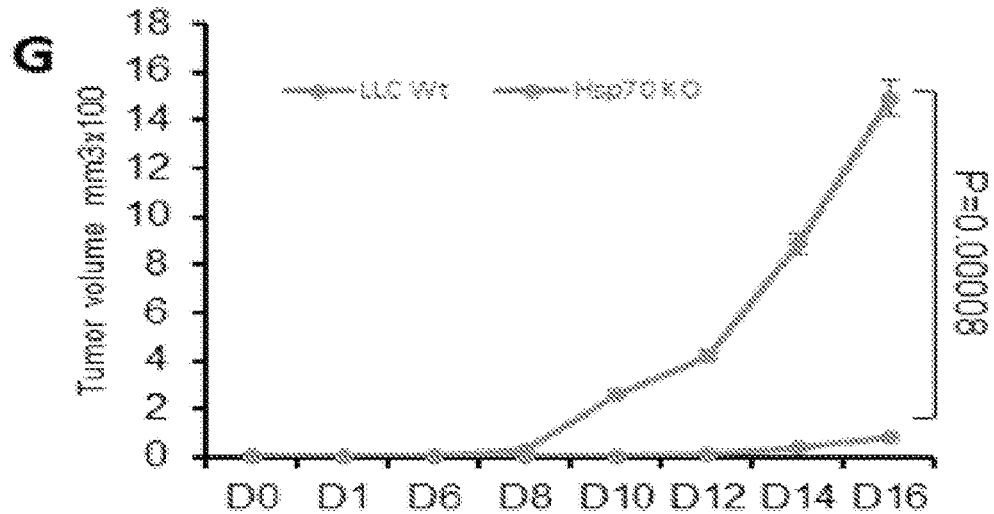

In further aspects, the present disclosure concerns the inhibition of expressed Hsp70 in reducing differentiation into macrophages. As identified herein, through silencing Hsp70 expression, the secretion of pHsp70 is reduced and/or inhibited. Hsp70 expression can be reduced through techniques such as RNA (ribonucleic acid) silencing through the administration of dsRNA (double-stranded RNA) such as siRNA (small interfering RNA) or shRNA (small hairpin RNA) using nucleotide sequences corresponding to mRNA sequences of transcribed Hsp70. As identified in the working examples herein, the reduced expression of Hsp70 in lung tumor cells led to strong decrease in MØ differentiation activity of the CM from tumor cells (see, e.g. FIG. 3).

Accordingly, in some aspects, the present disclosure concerns methods of silencing and/or reducing Hsp70 expression and/secretion from a tumor cell. In some aspects, the methods may include introducing a silencing RNA that includes a portion of the Hsp70 mRNA sequence. In some aspects, the silencing RNA may be double-stranded or a single self-annealing RNA strand. In further aspects, the double stranded portion(s) of the RNA or the self-annealing portions will correspond to a portion of the Hsp70 mRNA. The RNA may include synthetic or recombinant nucleic acids. The RNA may be transcribed in the tumor cell from a vector, such as a viral vector. In further aspects, the RNA may be a packaged and/or encapsulated RNA, such as a lipid encapsulated RNA. In some aspects, the RNA may be encapsulated in an ionizable lipid. In some aspects, the RNA may be encapsulated in lipid nanoparticles (LNPs) or lipid-like nanoparticles (LLNs). In some aspects, the RNA may be encapsulated in an LNP or LLN of two or more lipids.

In further aspects, the present disclosure concerns administration of NVs to a tumor or the TME in combination with silencing and/or reducing Hsp70 expression and/secretion from a tumor cell.

In other aspects, the present disclosure concerns methods to affect the polarization of macrophages by administration of NVs to the tumor cells or the TME and/or by silencing or inhibiting Hsp70 expression. Macrophages can be polarized into an M1 pro-inflammatory phenotype or an M2 pro-growth/proliferation phenotype. As identified herein, when Hsp70 expression is reduced and/or inhibited in tumor cells, the secretion thereof into the TME is similarly reduced. When Hsp70 expression was inhibited, intra-tumor MØs were assessed for their polarization status and it was identified that tumors from the control, i.e. non-knockdown, contained predominantly pro-tumorigenic M2 polarized MØs, while tumors from Hsp70 knockdown were reduced in size and contained M1 polarized MØs (see, e.g. FIG. 3). The studies presented herein demonstrate the significance of Hsp70 in the regulation of tumor MØ polarization and subsequent tumor growth. Accordingly, the present disclosure demonstrates that through inhibiting the expression and/secretion and/or phosphorylation of Hsp70, polarization of macrophages in the TME into an M2 phenotype can be prevented and/or M1 polarization can be increased and/or stimulated.

Figure 4:
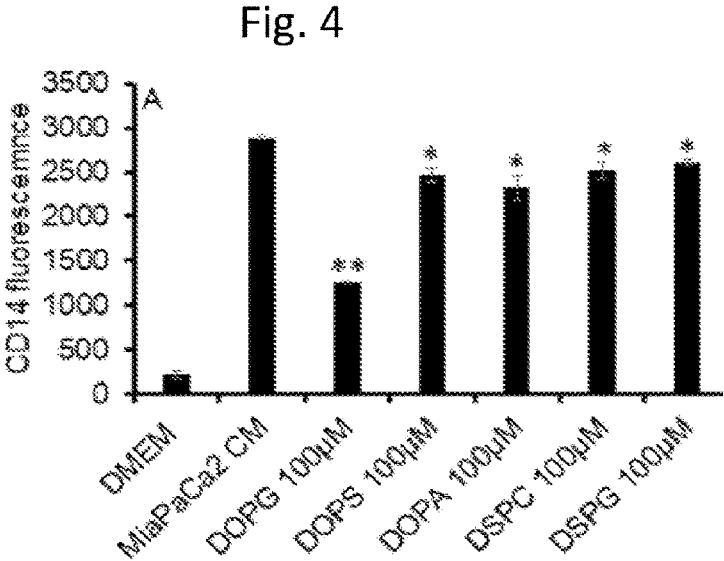
FIG. 4 shows DOPG NVs inhibit MiaPaCa2 CM and TLR2/TLR6 agonist induced THP1 differentiation. A shows DOPG NVs specifically inhibit MiaPaCa2 CM induced THP1 differentiation. B shows DOPG NVs inhibit MiaPaCa2 CM induced THP1 differentiation in a dose dependent manner. C shows the PLS used at indicated concentrations are non-toxic as evident by lack of propidium iodide uptake.
Figure 4:
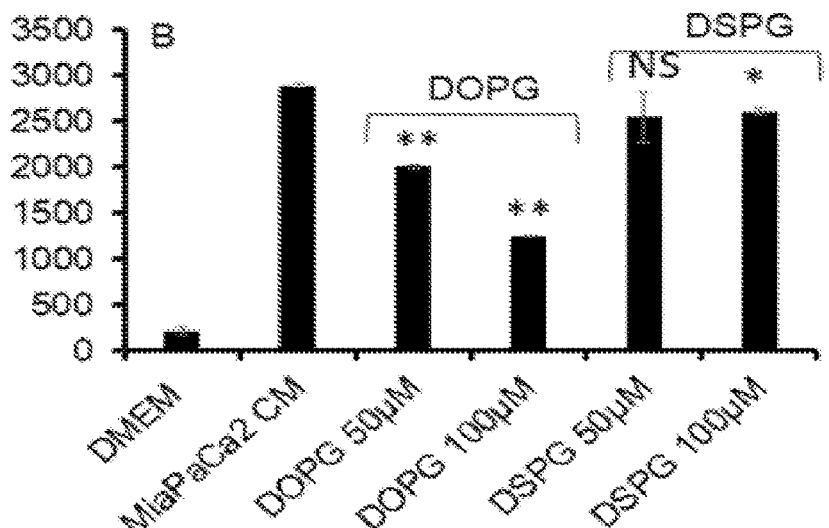
Figure 4:
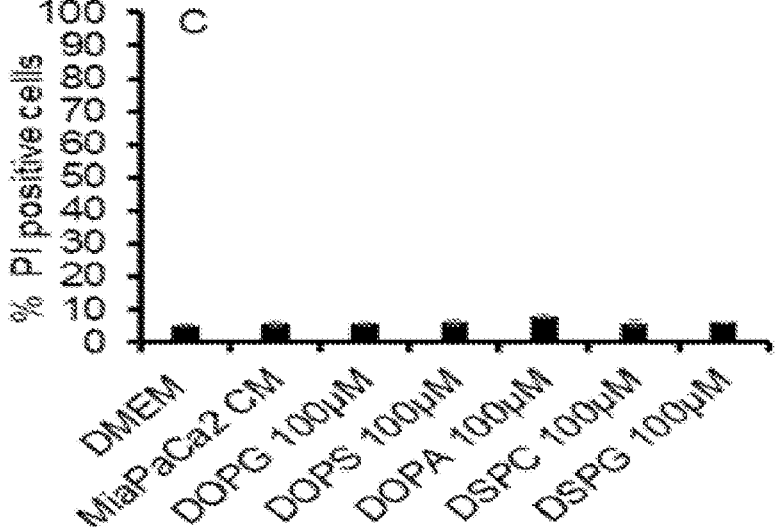

In some aspects, the present disclosure concerns the identification of compounds that inhibit the ability of pHsp70 to cause M2 polarization and/or that will stimulate or increase M1 polarization. In certain aspects, the present disclosure concerns the identification that nanovesicles (NVs) of DOPG can inhibit the activity of pHsp70 on the toll-like receptors (TLRs) of monocytes and/or macrophages and prevent the polarization thereof to M2 and/or stimulate M1 polarization. The presence of TLR2 and/or TLR6 on monocytes is involved in host innate defense by recognizing pathogen derived lipopeptides. Recent studies have identified a role for phospholipids (PLs) in innate immune responses by inhibition of inflammatory responses from MØs. Lipoteichoic acid (LTA) which binds to TLR2/TLR6 contains a glycerophosphate which was suggestive of a role for lipid-like compounds and especially glycerophosphate containing lipids in TLR binding and regulation. Furthermore, it has been found that cancer secreted pHsp70 acts through a macrophage heterodimer of TLR2/TLR6. Therefore, as set forth herein, different PLs were tested for their ability to block the monocyte TLR2/TLR6 pathway and thus inhibit monocyte differentiation. As set forth in the examples, nanovesicles (NVs) composed of a panel of PLs differing in saturation, head groups and area per lipid (APL) were analyzed for their capability to block monocyte differentiation induced by cancer CM. As also identified herein, DOPG NVs inhibited THP-1 differentiation induced by pancreatic tumor CM in a dose-dependent manner (see, FIG. 4). Among tested PLs, DOPG has the largest APL, which indicates that extent of unsaturation and APL contribute to the PL's inhibitory activity on monocyte differentiation. Since Hsp70 is the causal factor involved in MØ differentiation induced by cancer CM, analyses of DOPG NVs through LC-MS revealed binding of DOPG NVs to Hsp70.

Figure 5:
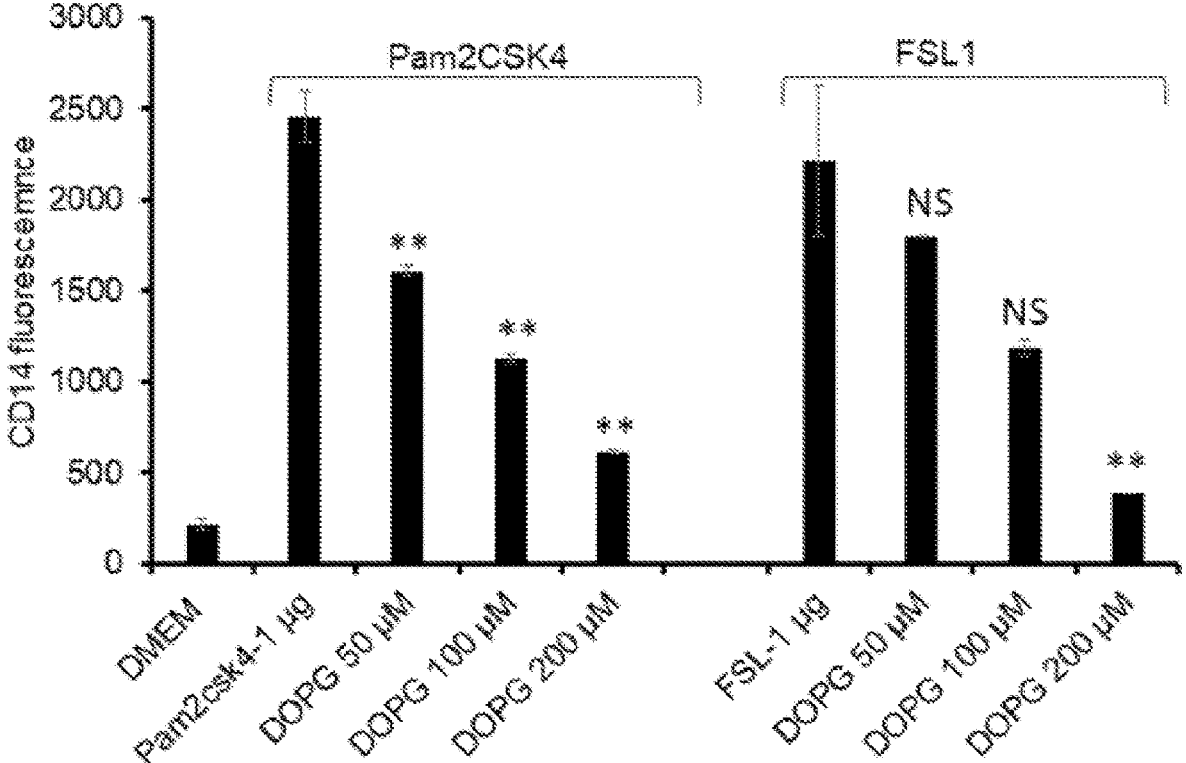
FIG. 5 shows DOPG NVs inhibit TLR2/TLR6 agonist induced THP1 differentiation. DOPG NVs inhibit THP1 differentiation induced by TLR2/TLR6 agonists Pam2CSK4 and FSL1
Figure 6:
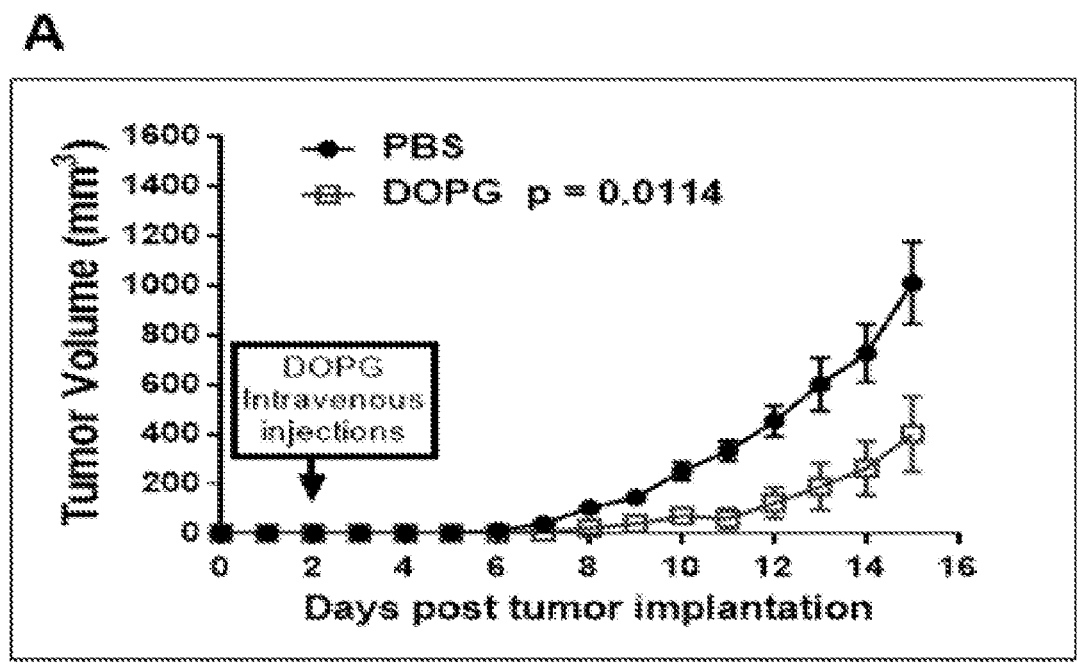
FIG. 6 shows DOPG NV treatment reduces tumor growth and tumor M2 macrophages. A shows administration of DOPG NVs intravenous into mice reduces LLC subcutaneous tumor growth in mice compared to PBS injection. B shows reduction in tumor M2 MØs in DOPG NV treated mice.
Figure 6:
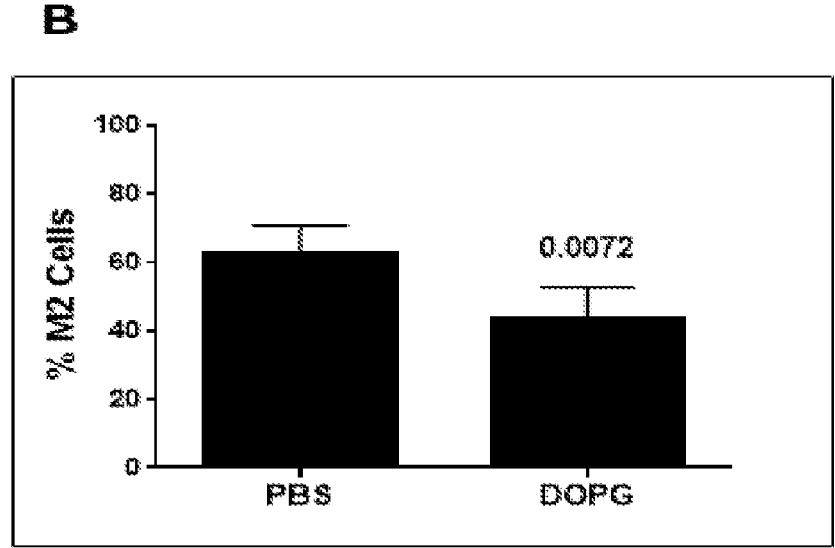

Further, since PLs interfere with TLR functions in controlling MØ inflammatory responses, the effect of DOPG-NVs on TLR2/TLR6 dependent differentiation of monocytes was tested in response to TLR2/TLR6-specific agonists. It was identified that incubation of monocytes cells with DOPG NVs prior to the addition of TLR2/TLR6 agonists led to a strong inhibition of differentiation (see, FIG. 5). This confirmed that DOPG NVs exhibit an inhibitory effect on the TLR2/TLR6 and that DOPG NVs effectively inhibit TLR2/TLR6 dependent monocyte differentiation. Since a strong inhibition of cancer CM-induced monocyte differentiation by DOPG NVs was observed, the efficacy of DOPG NVs on tumor growth in mouse subcutaneous tumors derived from LLC cells was tested. As shown in FIG. 6, DOPG-NV treatment of mice bearing tumors led to substantial reduction in tumor growth and reduction in tumor M2 MØ in DOPG NV-treated mice.

In some aspects, the present disclosure concerns the treatment of tumor cells and/or the TME with a lipid nanovesicle that includes the lipid DOPG. In some aspects, the NV may include two or more different lipids wherein at least on is DOPG. In other aspects, the NV may be entirely of DOPG.

In some aspects, the DOPG NVs may be administered in a therapeutically effective amount. As used herein, a "therapeutically effective amount" is used with reference to the treatment of cancers or cancerous cells as an amount that will decrease, reduce, inhibit, or otherwise abrogate the growth of a cancer cell or tumor. In some aspects, the therapeutic agent(s) can be delivered regionally to a particular affected region or regions of the subject's body. In some aspects, wherein such treatment is considered more suitable, the therapeutic agent(s) can be administered systemically. For example, the compound can be administered orally or parenterally. In certain aspects, a therapeutic agent is delivered intravenously.

In other aspects, DOPG NVs may be administered in combination with an inhibitor of Hsp70 expression, such as with an RNA that silences Hsp70 expression. In certain aspects, the DOPG NVs may be administered with a lipid nanoparticle that encapsulates an RNA targeting Hsp70 expression.

In some aspects of the present disclosure, methods of tumor-targeted delivery are provided that include the administration of DOPG coupled and/or co-administered with saposin C (SapC). Due to the effects identified with DOPG, it was identified that targeting the DOPG to tumor cells and/or the TME may be of further advantage. Accordingly, tumor targetable DOPG NVs were developed by assembling DOPG NVs together with SapC. SapC-DOPG therefore refers to a stable nanovesicle composition that is composed of saposin C (SapC), which is a lysosomal protein that catabolizes glycosphingolipids, and the phospholipid DOPG. In one aspect. SapC may include a peptide or polypeptide with an amino acid sequence that includes the sequence of SDVYCEVCEFLVKEVTKLIDNNK-TEKEILDAFDKMCSKLPKSLSEECQEVVDT YGSSIL-SILLEEVSPELVCSMLHLCSG (SEQ ID NO: 1). In some aspects, SapC may include an amino acid sequence having from about 75 to about 100% identity to SEQ ID NO: 1, including about 76, 77, 78, 79, 80, 81, 82, 83, 84, 85, 86, 87, 88, 89, 90, 91, 92, 93, 94, 95, 96, 97, 98, and 99% sequence identity to SEQ ID NO: 1.

Figure 8:
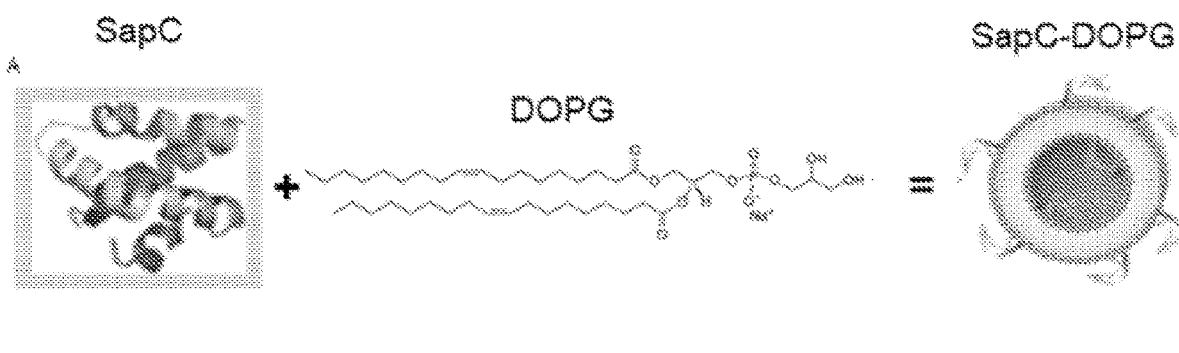
FIG. 8 shows targeting of SapC-DOPG NVs to the tumor site in a mouse glioblastoma model. A shows SapC-DOPG nanovesicles (NVs) target tumors. SapC has high affinity for cancer cell PS. Together with DOPG it forms NVs that target PS-rich domains on cancer cells. B shows SapC-DOPG NVs coupled to fluorescent dye CellVue Maroon (CVM) hones in on GBM tumors indicating precise brain tumor targeting (left panel) and tumor luminescence (right panel). Bottom panels show the 15 magnified brain region.
Figure 8:
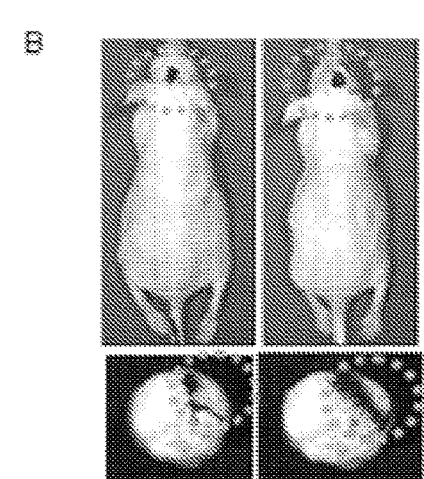

Since SapC is a tumor targeting molecule by virtue of its ability to bind phosphatidylserine (PS) exposed on tumor cells, when complexed with DOPG NVs, the SapC can direct SapC-DOPG NVs to the tumor site. As set forth herein, it was observed that precise targeting of SapC-DOPG NVs was achieved to the tumor site in a mouse glioblastoma model (See FIG. 8).

In some aspects, the present disclosure concerns DOPG NVs and SapC-DOPG NVs that inhibit monocyte differentiation and/or MØ polarization in the TME. For example, as set forth herein, NVs of the present disclosure can inhibit monocyte differentiation from glioblastoma CM and from pancreatic ductal adenocarcinoma (PDAC) CM and accordingly inhibit tumor growth. Further, the TLR2/TLR6 heterodimer on the surface of monocytes is involved in host innate defense by recognizing pathogen-derived lipopeptides (Yamamoto et al., *Gastroenterol Res Pract* 2010, 240365, 2010; Uematsu et al. *Handb Exp Pharmacol* 183, 1-20, 2008). Recent studies have identified a role for phospholipids (PLs) in innate immune responses by inhibition of inflammatory responses from MØs (Uematsu et al. *Handb Exp Pharmacol* 183, 1-20, 2008; Hashimoto et al., *J Biol Chem* 278, 44205-44213, 2003). Lipoteichoic acid (LTA) which binds to the TLR2/TLR6 heterodimer contains a glycerophosphate (Ginsburg, *Lancet* Infect Dis 2, 171-179, 2002). Furthermore, PLs have been shown to bind TLR ligands and inhibit activation of TLRs (Hashimoto et al., *J Biol Chem* 278, 44205-44213, 2003). Collectively, these point to a role for lipid-like compounds and especially glycerophosphate-containing lipids in TLR binding and regulation.

In some aspects, the present disclosure concerns administration of NVs to bind pHsp70 and/or inhibit activation of the TLR2/TLR6 heterodimer pathways and/or inhibit monocyte differentiation. As set forth herein, different PLs were tested for their ability to bind pHsp70 and block the monocyte TLR2/TLR6 heterodimer pathway and thereby inhibit monocyte differentiation, to thereby provide a PL-based immuno-therapies to block tumor cell induced MØ differentiation. As set forth herein, a panel of NVs differing in saturation, head groups and area per lipid (APL) were analyzed for their capability to block monocyte differentiation induced by tumor cell CM. Incubation of monocytes with non-toxic levels of DOPG NVs led to substantial inhibition of monocyte differentiation in a dose-dependent manner, without cellular toxicity (see FIG. 9). Among tested PLs, DOPG has the largest APL which indicates that the extent of unsaturation and APL contribute to the PL's inhibitory activity on monocyte differentiation. Accordingly,

9

Figure 9:
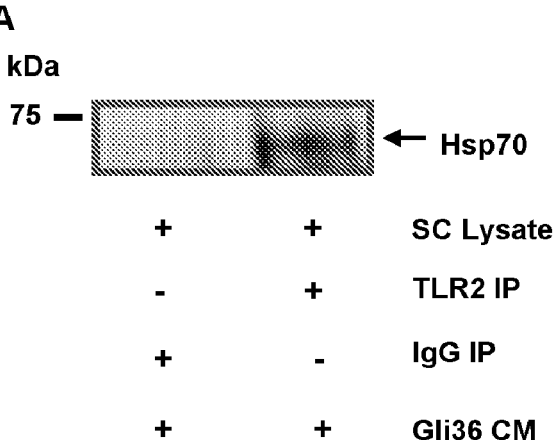
FIG. 9 shows cancer secreted Hsp70 interacts with TLR2 and tumor growth is reduced and intra-tumor M2 polarized MØs are reduced in TLR2$^{-/-}$ mice compared to WT mice. A shows Western blot showing presence of py-Hsp70 in the TLR2 immunoprecipitates of SC cell lysates incubated with Gli36 CM. B shows M2 MØ marker CD206 expression of peritoneal MØs in WT and TLR2–/– mice intraperitoneally injected with DMEM or Gli36 CM. C shows tumor growth curves of LLC-GFP subcutaneous tumors in WT and TLR2$^{-/-}$ mice. D shows expression of CD206 in tumor-MØs isolated from LLC-GFP subcutaneous tumors from WT and TLR2$^{-/-}$ mice analyzed by flow cytometry.
Figure 9:
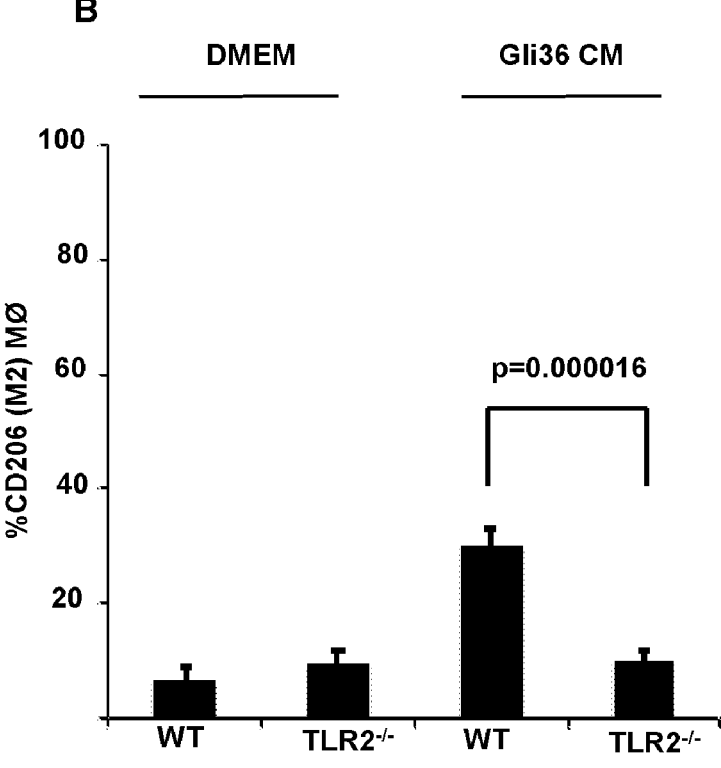
Figure 9:
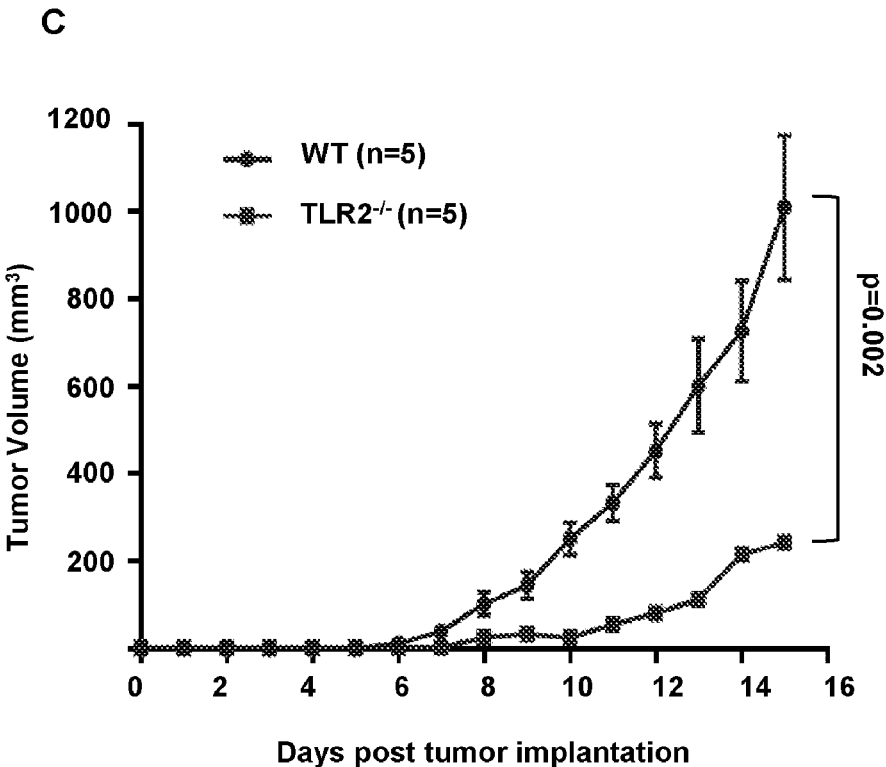
Figure 9:
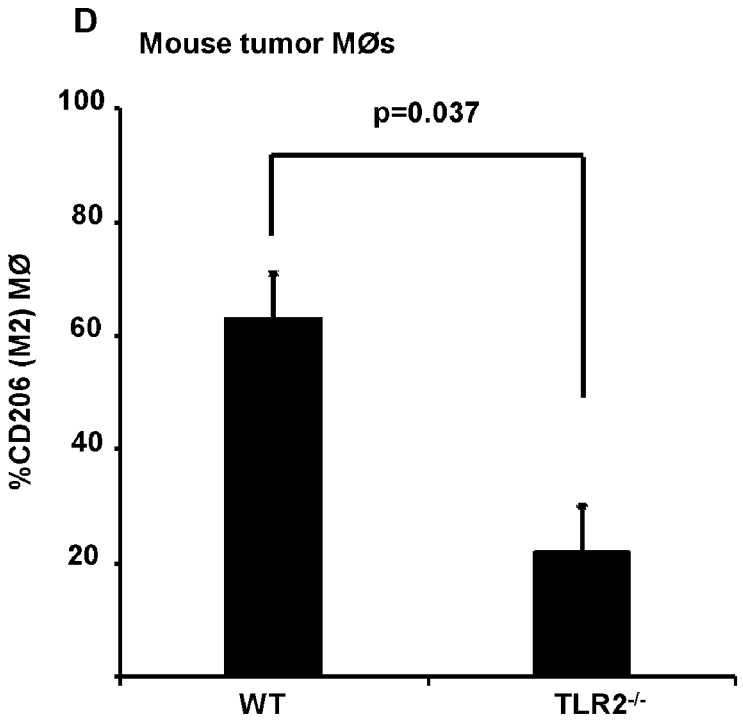

DOPG NVs, when injected intravenously into mice substantially reduced tumor growth compared to tumor growth in saline-injected mice, with significant reduction in M2 polarized tumor MØs (see FIG. 9). Therefore, DOPG NVs show efficacy as an immunotherapeutic agent to block monocyte differentiation, immunosuppressive M2 MØ polarization and inhibit tumor progression.

In some aspects, the present disclosure concerns methods for treating malignant, cancerous or abnormal cells through administration of DOPG and/or SapC-DOPG NVs as described herein. In some aspects the cells are pancreatic cells or are of pancreatic origin or lung cells or of lung origin or glial cells or of glial origin. In further aspects, the cells are abnormal or mutated or initiated such that they possess an ability for dysregulated and/or uncontrolled growth. In further aspects, the cells are in vitro, in vivo, ex vivo and/or ex situ for part of all of the methods as set forth herein.

In some aspects, the methods of the present disclosure concern treating or administration of the therapeutics described herein to a subject or a patient, such as a subject or a patient with a tumor and/or an abnormal or cancerous cell or population thereof. As used herein a "subject" or "patient" refers to a mammal. Optionally, a subject or patient is a human or non-human primate. Optionally, a subject or patient is a dog, cat, horse, sheep, cow, rabbit, pig, or mouse. In some aspects, the subject may be diagnosed with a tumor and/or suspected of having or possessing such within one or more organs or bodily systems or the subject may be selected for treatment as described herein based on a diagnosis or suspected diagnosis of a tumor within one or more organs and/or bodily systems. In other aspects, the subject may be unaware of the presence of a tumor or the tumor may be at a point of growth or progression such that it avoids detection. In further aspects, the methods of the present disclosure can be used prophylactically on a subject to prevent or alleviate any cell initiation, progression and/or promotion into a tumor or a precursor thereof.

In some aspects, the methods of the present disclosure concern treating or administration of the therapeutics described herein to a tumor and/or the TME. A tumor may refer to a mass or a collection of cancerous or abnormal cells that include cells having undergone an initiation step toward dysregulated growth and/or dysregulated cell death and/or apoptosis. In some aspects, a tumor may include one or more malignant cells and/or one or more metastatic cells.

In some aspects, the methods of the present disclosure concern administration and/or application of one or more doses of DOPG and/or SapC-DOPG. Each individual dose of DOPG and/or SapC-DOPG NVs may include an amount of from about 0.1 mg/kg to about 12.0 mg/kg DOPG and/or SapC-DOPG, including about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, and 11.9 mg/kg. In some aspects, an individual dose may include an amount of from about 0.2 mg/kg to about 3.0 mg/kg DOPG and/or SapC-DOPG. In other aspects, an individual dose may include an amount of from about 0.3 to about 1.2 mg/kg DOPG and/or SapC-DOPG.

In some aspects, DOPG and/or SapC-DOPG NVs may be administered separately or in combination, as well as a single dose or as multiple doses over a treatment period. A "treatment period" may refer to a length of time corresponding to a therapeutic treatment regimen. In some aspects, DOPG and/or SapC-DOPG is administered over a period of time ranging from days to weeks or months. In some aspects, a treatment period comprises from about 14 to about 40 consecutive days, including 15, 16, 17, 18, 19, 20, 21, 22, 23, 24, 25, 26, 27, 28, 29, 30, 31, 32, 33, 34, 35, 36, 37, 38, and 39 days. In some aspects, a therapeutically effective amount of DOPG and/or SapC-DOPG is administered in 10 to 15 doses over a twenty-eight day cycle. In an exemplary schedule, a dose of DOPG and/or SapC-DOPG is administered five times during the first week; three times during weeks two and three; and once during week four.

In further aspects, the method of the present disclosure can be combined with other treatments or therapies, such as radiation therapy. Administering a radiation therapy and administering the DOPG and/or SapC-DOPG can be accomplished in overlapping or alternating sequences. For example, a fraction of radiation may be administered to the patient on Day 1, then on Day 2, a fraction of radiation is administered to the patient together with a dose of DOPG and/or SapC-DOPG, Additionally, DOPG and/or SapC-DOPG may be administered to the patient on Day 1, and on Day 2 and Day 3 the patient is administered a radiation fraction.

In further aspects, DOPG and/or SapC-DOPG can be administered as a pharmaceutical composition and/or with a pharmaceutically acceptable carrier. A pharmaceutical composition may be in any dosage form suitable for administration to a subject, illustratively including solid, semi-solid and liquid dosage forms such as tablets, capsules, powders, granules, suppositories, pills, solutions, suspensions, ointments, lotions, creams, gels, pastes, sprays and aerosols. Liposomes and emulsions are further well-known types of pharmaceutical formulations that can be used to deliver a pharmaceutical agent. Pharmaceutical compositions may generally include a pharmaceutically acceptable carrier such as an excipient, diluent and/or vehicle. Delayed release formulations of compositions and delayed release systems, such as semipermeable matrices of solid hydrophobic polymers can be used. Similarly, DOPG and/or SapC-DOPG can be administered with a pharmaceutically acceptable carrier and/or an excipient. Such additives are understood in the art. For example, lists of such can be found in Remington: The Science and Practice of Pharmacy, $22^{nd}$ Ed., Pharmaceutical Press, 2012. Pharmaceutically acceptable carriers or excipients may include, but are not limited to, polymers, resins, plasticizers, fillers, lubricants, diluents, binders, disintegrants, solvents, co-solvents, buffer systems, surfactants, preservatives, sweetening agents, flavoring agents, pharmaceutical grade dyes or pigments, and viscosity agents.

In some aspects, the methods of the present disclosure can be used to treat any tumor or TME. In some aspects, the methods of the present disclosure can be applied to treat any form of cancer. In some aspects, the methods of the present disclosure can be used to treat a pancreatic cancer and/or a glioblastoma and/or a lung cancer. As set forth in the examples herein, the administration of DOPG and/or SapC-DOPG NVs to TME or CM from tumor cells of lung, glial, and pancreatic origin were effective in reducing local immunosuppression and/or reducing tumor progression and/or tumor growth.

In some aspects, the methods of the present disclosure concern combination or successive treatment with two or more pancreatic cancer agents or glioblastoma agents or lung cancer agents. In some aspects, the methods may include the administration of DOPG and/or SapC-DOPS with one or more of the agents selected from nab-paclitaxel, everolimus, erlotinib, 5-fluorouracil, irinotrecan, olaparib, mitomycin, paclitaxel, sunitinib, FOLFIRINOX, cisplatin, oxaliplatin, lanreotide, lutetium Lu 177-dotatate, or combinations thereof. In some aspects, the methods may include the administration of DOPG and/or SapC-DOPS with everolimus, bevacizumab, carmustine, naxitamab, lomustine, temozolomide, or combinations thereof. In some aspects, the methods may include the administration of DOPG and/or SapC-DOPS with paclitaxel, afatinib, everolimus, alectinib, pemetrexed, brigatinib, atezolizumab, bevacizumab, capmatinib, carboplatin, cemoplimab, ceritinib, crizotinib, ramucirumab, dabrafenib, docetaxel, doxorubicin, durvalumab, entrectinib, erlotinib, pralsetinib, gefitinib, gemcitabine, ipilimumab, pembrolizumab, lorlatinib, trametinib, methotrexate, necitumumab, nivolumab, osimertinib, selpercatinib, tepotinib, trametinib, vinorelbine, or combinations thereof. In some aspects, the methods may include the administration of DOPG and/or SapC-DOPS with an inhibitor of Hsp70 expression, such as with an RNA that silences Hsp70 expression. In certain aspects, the DOPG NVs may be administered with a lipid nanoparticle that encapsulates an RNA targeting Hsp70 expression.

ASPECTS

A first aspect of the disclosure, either alone or in combination with any other aspect set forth herein, concerns a method for treating a cancerous or pre-cancerous cell comprising administering to the cell a therapeutically effective amount of nanovesicles comprised of dioleoylphosphatidylglycerol (DOPG).

A second aspect of the disclosure, either alone or in combination with any other aspect set forth herein, concerns the method of the first aspect, wherein the nanovesicles further comprise saposin C (SapC).

A third aspect of the disclosure, either alone or in combination with any other aspect set forth herein, concerns the method of the second aspect, wherein a combination of DOPG and SapC-DOPG nanovesicles are administered.

A fourth aspect of the disclosure, either alone or in combination with any other aspect set forth herein, concerns the method of any of the first, second or third aspects, wherein the cell is in vitro.

A fifth aspect of the disclosure, either alone or in combination with any other aspect set forth herein, concerns the method of any of the first, second or third aspects, wherein the cell is in vivo.

A sixth aspect of the disclosure, either alone or in combination with any other aspect set forth herein, concerns the method of any of the first through fifth aspects, wherein the method further comprises administering an additional chemotherapeutic to the cell.

A seventh aspect of the disclosure, either alone or in combination with any other aspect set forth herein, concerns the method of the sixth aspect, wherein the additional chemotherapeutic is selected from the group consisting of everolimus, erlotinib, 5-fluorouracil, irinotrecan, olaparib, mitomycin, paclitaxel, sunitinib, FOLFIRINOX, cisplatin, oxaliplatin, lanreotide, lutetium Lu 177-dotatate, bevacizumab, carmustine, naxitamab, lomustine, temozolomide, afatinib, alectinib, pemetrexed, brigatinib, atezolizumab, capmatinib, carboplatin, cemoplimab, ceritinib, crizotinib, ramucirumab, dabrafenib, docetaxel, doxorubicin, durvalumab, entrectinib, pralsetinib, gefitinib, gemcitabine, ipilimumab, pembrolizumab, lorlatinib, trametinib, methotrexate, necitumumab, nivolumab, osimertinib, selpercatinib, tepotinib, trametinib, vinorelbine, or a combination thereof.

An eighth aspect of the disclosure, either alone or in combination with any other aspect set forth herein, concerns a method for treating cancer in a subject, comprising administering a combination of a therapeutically effective amount of nanovesicles comprised of dioleoylphosphatidylglycerol (DOPG) to the subject.

A ninth aspect of the disclosure, either alone or in combination with any other aspect set forth herein, concerns the method of the eighth aspect, wherein the nanovesicles further comprise SapC.

A tenth aspect of the disclosure, either alone or in combination with any other aspect set forth herein, concerns the method of the eighth or ninth aspects, further comprising administering an additional chemotherapeutic or therapy to the subject.

An eleventh aspect of the disclosure, either alone or in combination with any other aspect set forth herein, concerns the method of the tenth aspect, wherein the additional chemotherapeutic is selected from the group consisting of everolimus, erlotinib, 5-fluorouracil, irinotrecan, olaparib, mitomycin, paclitaxel, sunitinib, FOLFIRINOX, cisplatin, oxaliplatin, lanreotide, lutetium Lu 177-dotatate, bevacizumab, carmustine, naxitamab, lomustine, temozolomide, afatinib, alectinib, pemetrexed, brigatinib, atezolizumab, capmatinib, carboplatin, cemoplimab, ceritinib, crizotinib, ramucirumab, dabrafenib, docetaxel, doxorubicin, durvalumab, entrectinib, pralsetinib, gefitinib, gemcitabine, ipilimumab, pembrolizumab, lorlatinib, trametinib, methotrexate, necitumumab, nivolumab, osimertinib, selpercatinib, tepotinib, trametinib, vinorelbine, or a combination thereof A twelfth aspect of the disclosure, either alone or in combination with any other aspect set forth herein, concerns the method of the tenth aspect, wherein the additional therapy is selected from antibody therapy, gene silencing therapy, vaccine therapy, or radiation therapy.

A thirteenth aspect of the disclosure, either alone or in combination with any other aspect set forth herein, concerns the method of the eighth aspect, wherein the cancer is a pancreatic cancer.

A fourteenth aspect of the disclosure, either alone or in combination with any other aspect set forth herein, concerns the method of the eighth aspect, wherein the cancer is a glioblastoma.

A fifteenth aspect of the disclosure, either alone or in combination with any other aspect set forth herein, concerns the method of the eighth aspect, wherein the cancer is a lung cancer.

A sixteenth aspect of the disclosure, either alone or in combination with any other aspect set forth herein, concerns the method of the eighth or ninth aspect, wherein the nanovesicles are administered in a plurality of doses over a treatment period.

A seventeenth aspect of the disclosure, either alone or in combination with any other aspect set forth herein, concerns the method of the sixteenth aspect, wherein the treatment period comprises from about 14 to 40 consecutive days.

An eighteenth aspect of the disclosure, either alone or in combination with any other aspect set forth herein, concerns the method of the sixteenth or seventeenth aspect, wherein the nanovesicles are administered in a dose of from about 0.3 mg/kg to about 12 mg/kg.

EXAMPLES

Cancer Cells Secrete Phosphorylated Hsp70 (pHsp70) that
Triggers Macrophage Differentiation and M2 Polarization To reveal the molecular nature of cancer secreted mac-
rophage differentiation factor(s), we performed proteinase K
treatment of conditioned medium (CM) from Gli36 (glio-
blastoma) cells and tested the treated CM on THP-1 (mono-
cyte) cells. Interestingly, Proteinase K treatment led to
complete loss of THP-1 differentiation activity of Gli36CM,
indicating that the secreted activity is a protein (FIG. 1A). To
further identify the protein factor(s) secreted by cancer cells,
LC-MS analyses of the Gli36 CM was performed and many
proteins were found, of which select proteins with potential
in immune regulation were tested for their ability to induce
THP-1 differentiation (FIG. 1B). Quite interestingly, use of
monoclonal antibodies to deplete specific proteins from CM
led to the identification of Hsp70 as a candidate protein
involved in induction of MØ differentiation, as evident by
specific loss of THP-1 differentiation upon depletion of
Hsp70 from Gli36 CM (FIG. 3C). Whereas depletion of CM
with other monoclonal antibodies Enolase, Moesin, SSA or
IgG has no effect (FIG. 1C).

Figure 2:
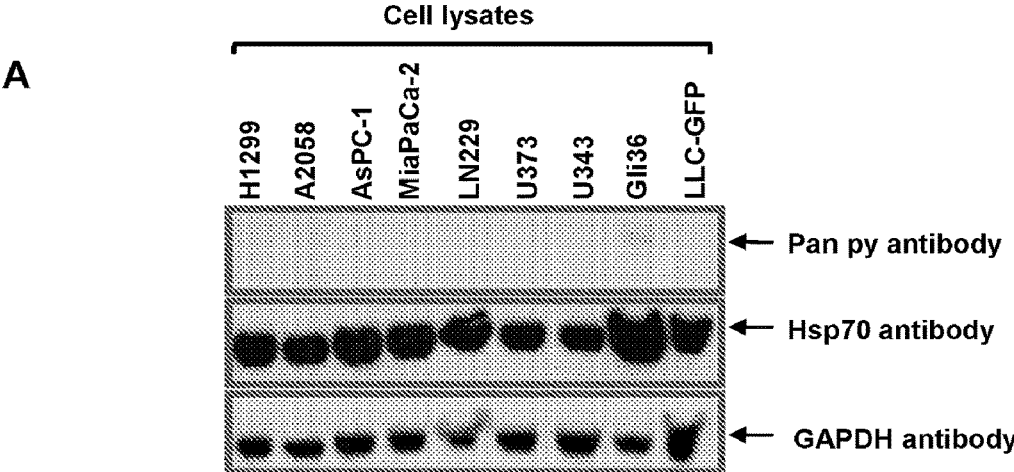
FIG. 2 shows cancer cells secreted Hsp70 is tyrosine phosphorylated (py-Hsp70) and phosphorylation is required for macrophage differentiation. A shows expression levels of Hsp70 in cell lysates and lack of py-Hsp70 in cellular lysates of cancer cells. B shows the presence of py-Hsp70 in immunoprecipitates of CM from indicated cancer cell lines. C). All of secreted Hsp70 is phosphorylated. D) Dephosphorylation of Hsp70 from Gli36 CM by using CIP and LP phosphatases. E). Dephosphorylated Gli36 CM fails to induce THP-1 differentiation.
Figure 2:
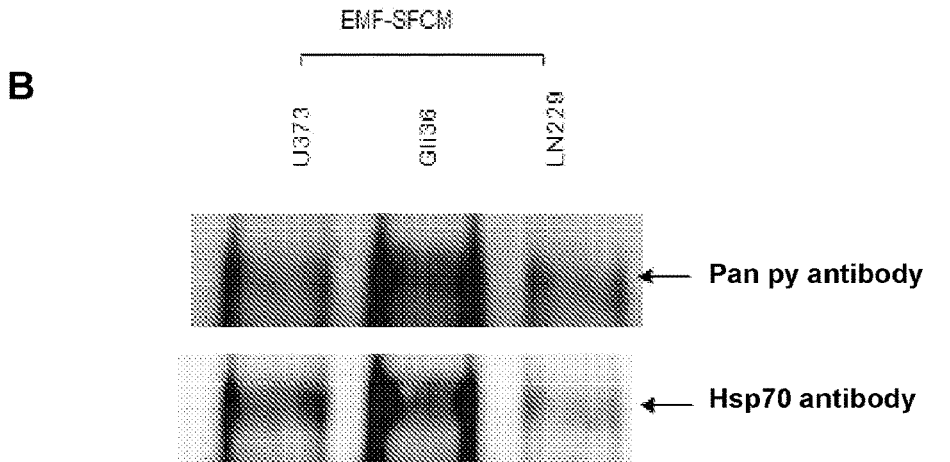
Figure 2:
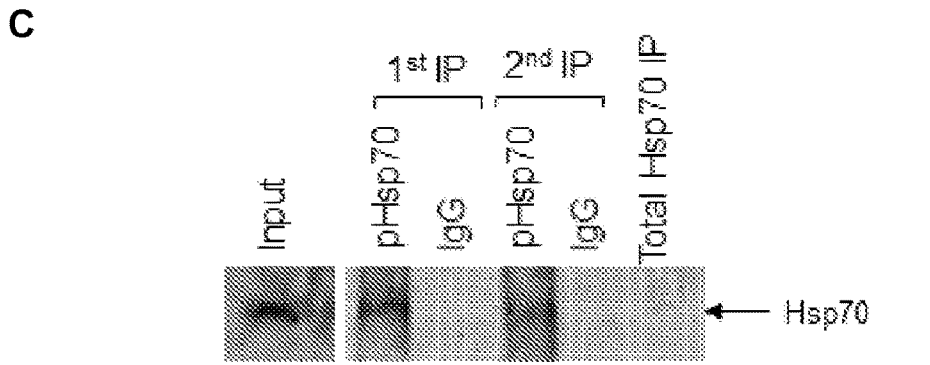
Figure 2:
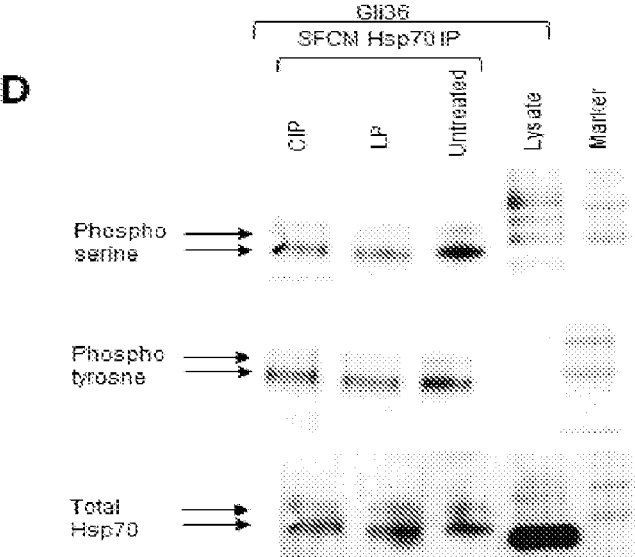
Figure 2:
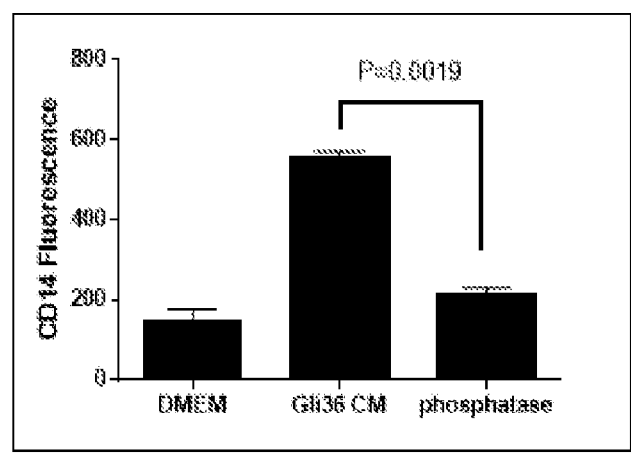

Since Hsp70 phosphorylation has been reported in prior
studies, assessment of phosphorylation status of Hsp70 from
cellular lysates of various cancer cells indicated that,
secreted Hsp70 is tyrosine-phosphorylated while intracellu-
lar Hsp70 is not tyrosine phosphorylated (FIGS. 2A & B).
Remarkably, the when CM from different cancer cell lines
was tested, Hsp70 is heavily phosphorylated as evident by
detection with phospho-tyrosine antibodies of total Hsp70
immunoprecipitates obtained from CM (FIG. 2B). To test
the extent of phosphorylation of secreted pHsp70, serial
immunoprecipitations of Gli36 CM were performed using
phospho-threonine specific Hsp70 antibody, to deplete
pHsp70 from Gli36 CM, followed by immunoprecipitation
with an antibody that recognizes Hsp70 irrespective of its
phosphorylation (anti-Hsp70 Ab). These studies revealed
that all of the secreted Hsp70 from Gli36 cells is phospho-
rylated, as evident by lack of Hsp70 in immunoprecipita-
tions obtained with anti-Hsp70 Ab (FIG. 2C). To test the
functional relevance of Hsp70 phosphorylation in MØ dif-
ferentiation, cancer cell CM was subjected to dephosphory-
lation by Calf intestinal phosphatase (CIP) and Lambda
phosphatase (LP). Both LP and CIP caused partial dephos-
phorylation of Hsp70 from CM (FIG. 2D). Next the CIP
treated CM from Gli36 cells was tested for its ability to
trigger THP-1 differentiation. Strikingly, dephosphorylation
of Gli36 CM by CIP treatment, led to strong decrease in
THP-1 differentiation compared to untreated Gli36 CM,
suggestive of the importance of Hsp 70 phosphorylation in
the MØ differentiation ability (FIG. 2E).

Hsp70 Knockdown in Cancer Cells Impairs Cancer Cell
Induced MØ Differentiation, Tumor Growth in Mice and
Alters Intra-Tumor MØ Polarization Next, to directly test the requirement of Hsp70 for cancer
induced MØ differentiation and polarization and subsequent
influence on tumor growth, Hsp70 knockdown in LLC (lung
tumor) and LN229 (glioblastoma cells) cells was performed
by lentiviral mediated expression of either control ShRNAs
or ShRNAs targeting Hsp70. Knockdown of Hsp70 led to
strong decrease in MØ differentiation activity of the CM
obtained from LLC and LN229 cells compared to CM
obtained from control ShRNA expressing cells, as evident
by strong reduction in CD14 expression on THP-1 cells
(FIGS. 3A&B). Of note, when implanted subcutaneously
into mice, tumor growth was severely impaired from LLC cells with Hsp70 knockdown, compared to LLC cells with
control ShRNAs (FIG. 3G). Most importantly, when intra-
tumor MØs were assessed for their polarization status,
tumors from LLC cells with control ShRNAs, contained
predominantly pro-tumorigenic M2 polarized MØs, while
tumors from Hsp70 knockdown are very small and con-
tained M1 polarized MØs (FIG. 3C-F). These findings
clearly indicate the importance of Hsp70 in the regulation of
tumor MØ polarization and subsequent tumor growth.

DOPG NVs Block Cancer CM-Induced Monocyte Differ-
entiation.

The TLR2/TLR6 on monocytes is involved in host innate
defense by recognizing pathogen derived lipopeptides.
Recent studies reveal a role for PLs in innate immune
responses by inhibition of inflammatory responses from
MØs. Lipoteichoic acid (LTA) which binds to TLR2/TLR6
contains a glycerophosphate. This suggests a potential role
for lipid-like compounds and especially glycerophosphate
containing lipids in TLR binding and regulation. Further-
more, it was found that cancer secreted pHsp70 acts through
macrophage TLR2/TLR6 heterodimer. Therefore, different
PLs were tested for their ability to block the monocyte
TLR2/TLR6 pathway and thus inhibit monocyte differen-
tiation. Nanovesicles (NVs) composed of a panel of PLs
differing in saturation, head groups and area per lipid (APL),
were analyzed for their capability to block monocyte dif-
ferentiation induced by cancer CM. Quite interestingly,
DOPG NVs inhibited THP-1 differentiation induced by
MiaPaCa-2 (pancreas) CM in a dose-dependent manner
(FIG. 4A-C), in comparison to the mild inhibition by other
PLs. Among these PLs, DOPG has the largest APL (DOPG
70.8 Å²>DOPS 65·3 Å²>DOPA 54.0 Å²), which indicates
that the extent of unsaturation and APL contribute to the
PL's inhibitory activity on monocyte differentiation.

Since Hsp70 is the causal factor involved in MØ differ-
entiation induced by cancer CM, analyses of DOPG NVs
through LC-MS revealed binding of DOPG NVs to Hsp70.
Further, since PLs interfere with TLR functions in control-
ling MØ inflammatory responses, the effect of DOPG-NVs
on TLR2/TLR6 dependent differentiation of THP1 was
tested in response to TLR2/TLR6-specific agonists,
Pam2CSK4 and FSL. It was found that incubation of THP-1
cells with DOPG NVs prior to the addition of TLR2/TLR6
agonists Pam2CSK4 and FSL led to a strong inhibition of
differentiation (FIG. 5). This confirms that DOPG NVs
exhibit an inhibitory effect on the TLR2/TLR6. These find-
ings indicate that DOPG NVs effectively inhibit TLR2/
TLR6 dependent monocyte differentiation. Since strong
inhibition of cancer CM-induced monocyte differentiation
by DOPG NVs was observed, the efficacy of DOPG NVs on
tumor growth in mouse subcutaneous tumors derived from
LLC cells was tested. As shown in FIG. 6, DOPG-NV
treatment of mice bearing LLC tumors led to substantial
reduction in tumor growth (FIG. 6A) and reduction in tumor
M2 MØ in DOPG NV-treated mice compared to PBS treated
mice (FIG. 6B).

Cancer Secreted Phospho Hsp70 Acts Through MØ TLR2 to
Induce MØ M2 Polarization and TLR2 is Required for
Tumor Growth and Intra-Tumor M2 MØs.

Hsp70 is known to bind TLRs. Therefore, it was exam-
ined whether py-Hsp70 directly binds to TLR2. To test this,
TLR2 was immunoprecipitated from SC MØs and incubated
with Gli36 CM. Western blots showed presence of Hsp70 in
TLR2 immunoprecipitates, suggesting the interaction of
py-Hsp70 with TLR2 (FIG. 9A). To further investigate the
TLR2 requirement in vivo for Gli36 CM-induced MØ
polarization, Gli36 CM was injected into peritonea of WT or TLR2$^{-/-}$ mice. 24 hrs later peritoneal MØs were isolated and analyzed by flow cytometry. As shown in FIG. 9B, Gli36 CM induction of peritoneal MØ M2 polarization was significantly reduced in TLR2 null mice compared to WT mice. Since there was an interaction between py-Hsp70 and TLR2, and since MØ M2 polarization in response to cancer CM was reduced in TLR2$^{-/-}$ mice, requirement of TLR2 for tumor growth and tumor MØ polarization was tested in mice. To achieve this, the mouse lung cancer cell line LLC-GFP cells were subcutaneously implanted in WT mice and TLR2 null mice and growth and MØ polarization were monitored. As presented in FIG. 9C, tumor growth in TLR2 null mice is slower compared to WT mice. Furthermore, the percentage of intra-tumor M2 polarized MØs was substantially reduced in TLR2 null mice (FIG. 9D). These data indicate the importance of TLR2 in MØ polarization in tumor growth control.

In summary, a novel immunotherapeutic agent DOPG-NVs is identified that acts to block cancer induced immunosuppression due its ability to bind cancer secreted pHsp70 and interference with TLR2/TLR6 heterodimer function. Since DOPG-NVs bind pHsp70 in TME as well as in circulation, DOPG-NVs are of potent efficacy in inhibiting primary tumors as well as metastases.

Treatment with SapC-DOPG

The experiments herein demonstrated that (1) DOPG NVs bind cancer secreted Hsp70 and inhibit MiaPaCa-2 conditioned media (CM)-induced MØ differentiation and (2) DOPG NVs reduce tumor growth when injected systemically into mice intravenously, even without targeted delivery. Therefore, it was expected that tumor-targeted delivery of DOPG NVs will have much stronger impact on tumor growth. Accordingly, tumor targetable DOPG NVs were developed by assembling DOPG NVs together with SapC. Since SapC is a tumor targeting molecule, by virtue of its ability to bind PS exposed on tumor cells, when in complex with DOPG NVs, it is expected to drive SapC-DOPG to the tumor site (as with SapC-DOPS). Indeed, in preliminary experiments observed precise targeting of SapC-DOPG NVs to the tumor site in a mouse glioblastoma model (See FIG. 7). DOPG can be coupled to CellVue Maroon (CVM), a fluorescent lipophilic dye, to track the SapC-DOPG-CVM NVs. Precise localization of SapC-DOPG-CVM NVs to the GBM tumor site was observed.

DOPG NVs block PDAC CM-induced monocyte differentiation and inhibit tumor growth in mice.

The TLR2/TLR6 heterodimer on monocytes is involved in host innate defense by recognizing pathogen-derived lipopeptides. Recent studies reveal a role for phospholipids (PLs) in innate immune responses by inhibition of inflammatory responses from MØs. Lipoteichoic acid (LTA) which binds to TLR2/TLR6 heterodimer contains a glycerophosphate. Furthermore, PLs have been shown to bind TLR ligands and inhibit activation of TLRs. This suggests a potential role for lipid-like compounds and especially glycerophosphate-containing lipids in TLR binding and regulation. Therefore, different PLs were tested for their ability to bind pHsp70 and block the monocyte TLR2/TLR6 heterodimer pathway and thereby inhibit monocyte differentiation, with the ultimate goal to develop PL-based immuno-therapies to block PDAC induced MØ differentiation.

Carefully prepared NVs (NVs) composed of a panel of PLs differing in saturation, head groups and area per lipid (APL), were analyzed for their capability to block monocyte differentiation induced by PDAC CM. Quite interestingly, incubation of THP-1 cells with MiaPaCa-2 CM with non-toxic levels of DOPG NVs led to substantial inhibition of THP-1 differentiation induced by MiaPaCa-2 CM in a dose-dependent manner, without cellular toxicity, in comparison to the mild inhibition by other PL NVs (FIGS. 4A-4C). Among the tested PLs, DOPG has the largest APL (DOPG; 70·8 Å$^2$>DOPS; 65·3 Å$^2$>DOPA; 54.0 Å$^2$), which indicates that the extent of unsaturation and APL contribute to the PL's inhibitory activity on monocyte differentiation. Accordingly, DOPG NVs, when injected intravenously into mice substantially reduced tumor growth compared to tumor growth in saline-injected mice, with significant reduction in M2 polarized tumor MØs (FIGS. 6A and 6B). Therefore, we anticipate that DOPG can be developed into immunotherapeutic agent to block monocyte differentiation, immunosuppressive M2 MØ polarization and inhibit PDAC progression.

The foregoing description of several aspects has been presented for purposes of illustration. It is not intended to be exhaustive or to limit the application to the precise forms disclosed, and obviously many modifications and variations are possible in light of the above teaching. It is understood that the disclosure may be practiced in ways other than as specifically set forth herein without departing from the scope of the disclosure. Any patents or publications mentioned in this specification are incorporated herein by reference to the same extent as if each individual publication is specifically and individually indicated to be incorporated by reference.

---

---

The invention claimed is:

1. A method for treating a cancerous or pre-cancerous cell comprising administering to the cell a therapeutically effective amount of lipid nanovesicles, wherein the lipid consists of dioleoylphosphatidylglycerol (DOPG).

2. The method of claim 1, wherein the nanovesicles are complexed with saposin C (SapC) to provide SapC-DOPG nanovesicles.

3. The method of claim 2, wherein a combination of DOPG and SapC-DOPG nanovesicles are administered.

4. The method of claim 1, wherein the cell is in vitro.

5. The method of claim 1, wherein the cell is in vivo.

6. The method of claim 1, wherein the method further comprises administering an additional chemotherapeutic agent to the cell.

7. The method of claim 6, wherein the additional chemotherapeutic agent is selected from the group consisting of everolimus, erlotinib, 5-fluorouracil, irinotrecan, olaparib, mitomycin, paclitaxel, sunitinib, FOLFIRINOX, cisplatin, oxaliplatin, lanreotide, lutetium Lu 177-dotatate, bevacizumab, carmustine, naxitamab, lomustine, temozolomide, afatinib, alectinib, pemetrexed, brigatinib, atezolizumab, capmatinib, carboplatin, cemoplimab, ceritinib, crizotinib, ramucirumab, dabrafenib, docetaxel, doxorubicin, durvalumab, entrectinib, pralsetinib, gefitinib, gemcitabine, ipilimumab, pembrolizumab, lorlatinib, trametinib, methotrexate, necitumumab, nivolumab, osimertinib, selpercatinib, tepotinib, trametinib, vinorelbine, or a combination thereof.

8. A method for treating cancer in a subject, comprising administering to the subject a therapeutically effective amount of lipid nanovesicles, wherein the lipid consists of dioleoylphosphatidylglycerol (DOPG).

9. The method of claim 8, wherein the nanovesicles are complexed with saposin C (SapC) to provide SapC-DOPG nanovesicles.

10. The method of claim 8, further comprising administering an additional chemotherapeutic agent or therapy to the subject.

11. The method of claim 10, wherein the additional chemotherapeutic agent is selected from the group consisting of everolimus, erlotinib, 5-fluorouracil, irinotrecan, olaparib, mitomycin, paclitaxel, sunitinib, FOLFIRINOX, cisplatin, oxaliplatin, lanreotide, lutetium Lu 177-dotatate, bevacizumab, carmustine, naxitamab, lomustine, temozolomide, afatinib, alectinib, pemetrexed, brigatinib, atezolizumab, capmatinib, carboplatin, cemoplimab, ceritinib, crizotinib, ramucirumab, dabrafenib, docetaxel, doxorubicin, durvalumab, entrectinib, pralsetinib, gefitinib, gemcitabine, ipilimumab, pembrolizumab, lorlatinib, trametinib, methotrexate, necitumumab, nivolumab, osimertinib, selpercatinib, tepotinib, trametinib, vinorelbine, or a combination thereof.

12. The method of claim 10, wherein the additional therapy is selected from antibody therapy, gene silencing therapy, vaccine therapy, or radiation therapy.

13. The method of claim 8, wherein the cancer is a pancreatic cancer.

14. The method of claim 8, wherein the cancer is a glioblastoma.

15. The method of claim 8, wherein the cancer is a lung cancer.

16. The method of claim 8, wherein the nanovesicles are administered in a plurality of doses over a treatment period.

17. The method of claim 16, wherein the treatment period comprises from about 14 to 40 consecutive days.

18. The method of claim 16, wherein the nanovesicles are administered in a dose of from about 0.3 mg/kg to about 12 mg/kg.

19. A method of treating glioblastoma in a subject in need thereof, the method comprising administering to the subject an effective amount of a lipid nanovesicle complex consisting of dioleoylphosphatidylglycerol (DOPG) complexed with saposin C (SapC).

* * * * *